United States Patent
Boileau et al.

(10) Patent No.: US 9,597,128 B2
(45) Date of Patent: Mar. 21, 2017

(54) SURGICAL TECHNIQUE AND APPARATUS FOR PROXIMAL HUMERAL FRACTURE REPAIR

(71) Applicant: Tornier, Montbonnot Saint Martin (FR)

(72) Inventors: Pascal Boileau, Nice (FR); Loïc Barouch, Carisieu (FR); Armodios Hatzidakis, Denver, CO (US); Edward Fehringer, Columbus, NE (US); Jean-Marie Berger, Eden Prairie, MN (US); Brian C. Hodorek, Winona Lake, IN (US)

(73) Assignee: Tornier, Inc., Edina, MN (US)

( * ) Notice: Subject to any disclaimer, the term of this patent is extended or adjusted under 35 U.S.C. 154(b) by 27 days.

(21) Appl. No.: 14/270,312

(22) Filed: May 5, 2014

(65) Prior Publication Data

US 2014/0243827 A1  Aug. 28, 2014

Related U.S. Application Data

(62) Division of application No. 12/990,772, filed as application No. PCT/IB2009/053468 on May 6, 2009, now abandoned.

(Continued)

(51) Int. Cl.
*A61B 17/56* (2006.01)
*A61B 17/72* (2006.01)

(52) U.S. Cl.
CPC .......... *A61B 17/7241* (2013.01); *A61B 17/72* (2013.01); *A61B 17/7233* (2013.01)

(58) Field of Classification Search
CPC .............................. A61B 17/72; A61B 17/7233

(Continued)

(56) References Cited

U.S. PATENT DOCUMENTS 5,472,444 A * 12/1995 Huebner ............ A61B 17/7283
606/62
5,766,174 A * 6/1998 Perry ................. A61B 17/1725
606/62

(Continued)

FOREIGN PATENT DOCUMENTS

DE  29916803  12/1999
EP  1685803   8/2006
EP  1779795   5/2007

OTHER PUBLICATIONS

Final Office Action for U.S. Appl. No. 12/990,772 dated Nov. 6, 2013 in 8 pages.

(Continued)

*Primary Examiner* — Ellen C Hammond
*Assistant Examiner* — Stuart S Bray
(74) *Attorney, Agent, or Firm* — Knobbe, Martens, Olson & Bear, LLP (57) ABSTRACT

A method and apparatus of reattaching a bone fragment to a proximal humerus of a humerus in a shoulder joint. The method includes introducing a distal end of the humeral nail into a medullary canal of the humerus. A first proximal screw is engaged with the bone fragment and a first proximal bore in the proximal end of the humeral nail to move the bone fragment toward the proximal humerus. The humeral nail and the attached bone fragment are rotated relative to the medullary canal of the humerus to position the bone fragment to an anatomically optimal location. The bone fragment is preferably one of a greater or lesser tuberosity of the proximal humerus. The method and apparatus can be used to reattach bone fragments in a variety of other joints.

20 Claims, 5 Drawing Sheets

Related U.S. Application Data (60) Provisional application No. 61/051,320, filed on May 7, 2008.

(58) Field of Classification Search
USPC .................................. 606/61, 62, 64, 66–67
See application file for complete search history.

(56) References Cited

U.S. PATENT DOCUMENTS

| | | | | |
|---|---|---|---|---|
| 5,779,705 | A * | 7/1998 | Matthews | A61B 17/7233 606/62 |
| 6,123,708 | A * | 9/2000 | Kilpela | A61B 17/72 606/62 |
| 6,296,645 | B1 | 10/2001 | Hover et al. | |
| 7,410,488 | B2 | 8/2008 | Janna et al. | |
| 7,608,075 | B2 * | 10/2009 | Tornier | 606/64 |
| 7,763,021 | B2 * | 7/2010 | Cole | A61B 17/72 606/64 |
| 7,763,023 | B2 * | 7/2010 | Gotfried | A61B 17/1721 606/62 |
| 7,909,825 | B2 | 3/2011 | Saravia et al. | |
| 7,914,532 | B2 | 3/2011 | Shaver et al. | |
| 8,157,802 | B2 | 4/2012 | Elghazaly et al. | |
| 8,394,103 | B2 * | 3/2013 | O'Reilly | A61B 17/1615 606/102 |
| 8,435,238 | B2 * | 5/2013 | Dejardin | A61B 17/1725 606/62 |
| 8,460,294 | B2 * | 6/2013 | Overes | A61B 17/7241 606/62 |
| 8,486,072 | B2 * | 7/2013 | Haininger | A61B 17/72 606/64 |
| 2002/0058948 | A1 * | 5/2002 | Arlettaz | A61B 17/1725 606/98 |
| 2003/0050704 | A1 * | 3/2003 | Keynan | A61B 17/72 623/22.12 |
| 2004/0049192 | A1 * | 3/2004 | Shimizu | A61B 17/7098 606/62 |
| 2004/0172026 | A1 * | 9/2004 | Ekholm | A61B 17/72 606/62 |
| 2005/0187550 | A1 * | 8/2005 | Grusin | A61B 17/72 606/62 |
| 2005/0273103 | A1 | 12/2005 | Wahl et al. | |
| 2006/0069392 | A1 | 3/2006 | Renzi Brivio et al. | |
| 2006/0084997 | A1 | 4/2006 | Dejardin | |
| 2006/0084999 | A1 | 4/2006 | Aschmann | |
| 2006/0095039 | A1 | 5/2006 | Mutchler | |
| 2006/0098851 | A1 * | 5/2006 | Shoham | A61B 17/1703 382/128 |
| 2006/0100623 | A1 * | 5/2006 | Pennig | A61B 17/72 606/64 |
| 2006/0106384 | A1 | 5/2006 | Reber et al. | |
| 2006/0106385 | A1 * | 5/2006 | Pennig | A61B 17/72 606/64 |
| 2006/0111717 | A1 | 5/2006 | Saueressig et al. | |
| 2006/0173457 | A1 * | 8/2006 | Tornier | A61B 17/72 606/62 |
| 2006/0189987 | A1 * | 8/2006 | Orbay | A61B 17/1721 606/62 |
| 2006/0200141 | A1 | 9/2006 | Janna et al. | |
| 2006/0200142 | A1 * | 9/2006 | Sohngen | A61B 17/72 606/62 |
| 2006/0235402 | A1 * | 10/2006 | Celli | A61B 17/746 606/293 |
| 2006/0241605 | A1 | 10/2006 | Schlienger et al. | |
| 2007/0016203 | A1 | 1/2007 | Schlienger et al. | |
| 2007/0123873 | A1 * | 5/2007 | Czartoski | A61B 17/72 606/62 |
| 2007/0123874 | A1 | 5/2007 | Czartoski et al. | |
| 2007/0123875 | A1 * | 5/2007 | Czartoski | A61B 17/744 606/62 |
| 2007/0123876 | A1 * | 5/2007 | Czartoski | A61B 17/72 606/62 |
| 2007/0123878 | A1 * | 5/2007 | Shaver | A61B 17/72 606/64 |
| 2007/0173834 | A1 * | 7/2007 | Thakkar | A61B 17/7208 606/62 |
| 2007/0219636 | A1 * | 9/2007 | Thakkar | A61B 17/1721 623/18.11 |
| 2007/0233104 | A1 * | 10/2007 | Metzinger | A61B 17/7241 606/62 |
| 2007/0255283 | A1 | 11/2007 | Ekholm et al. | |
| 2007/0265628 | A1 * | 11/2007 | Kraus et al. | A61B 17/72 606/64 |
| 2007/0270848 | A1 * | 11/2007 | Lin | A61B 17/746 606/65 |
| 2007/0276385 | A1 * | 11/2007 | Schlienger et al. | A61B 17/72 606/71 |
| 2007/0288016 | A1 * | 12/2007 | Halder | A61B 17/7225 606/62 |
| 2007/0288017 | A1 * | 12/2007 | Kaup | A61B 17/72 606/62 |
| 2007/0288019 | A1 * | 12/2007 | Schlienger | A61B 17/72 606/64 |
| 2007/0299447 | A1 * | 12/2007 | Watanabe | A61B 17/164 606/71 |
| 2008/0009869 | A1 * | 1/2008 | Schlienger | A61B 17/72 606/64 |
| 2008/0043307 | A1 | 2/2008 | Hayashi et al. | |
| 2008/0058814 | A1 * | 3/2008 | Gotfried | A61B 17/1717 606/62 |
| 2008/0088752 | A1 | 4/2008 | Kim et al. | |
| 2008/0119856 | A1 | 5/2008 | Gotfried | |
| 2008/0125818 | A1 * | 5/2008 | Sidebotham | A61B 17/72 606/329 |
| 2008/0147066 | A1 | 6/2008 | Longsworth et al. | |
| 2008/0183171 | A1 * | 7/2008 | Elghazaly | A61B 17/744 606/64 |
| 2008/0188853 | A1 | 8/2008 | Ferrante et al. | |
| 2008/0195098 | A1 | 8/2008 | Gotfried | |
| 2008/0221574 | A1 | 9/2008 | Cavallazzi et al. | |
| 2008/0221577 | A1 * | 9/2008 | Elghazaly | A61B 17/744 606/64 |
| 2008/0262496 | A1 * | 10/2008 | Schlienger | A61B 17/72 606/62 |
| 2008/0269751 | A1 * | 10/2008 | Matityahu | A61B 17/1725 606/64 |
| 2008/0281326 | A1 * | 11/2008 | Watanabe | A61B 17/164 606/62 |
| 2008/0287949 | A1 * | 11/2008 | Keith | A61B 17/7233 606/62 |
| 2008/0294164 | A1 * | 11/2008 | Frank | A61B 17/744 606/64 |
| 2008/0300597 | A1 * | 12/2008 | Morgan | A61B 5/0031 606/62 |
| 2009/0043307 | A1 * | 2/2009 | Faccioli | A61B 17/72 606/62 |
| 2009/0088752 | A1 * | 4/2009 | Metzinger | A61B 17/7283 606/62 |
| 2009/0157078 | A1 * | 6/2009 | Mikol | A61B 17/864 606/62 |
| 2009/0177240 | A1 * | 7/2009 | Perez | A61B 17/7233 606/86 R |
| 2009/0182336 | A1 * | 7/2009 | Brenzel | A61B 17/7225 606/62 |
| 2009/0209961 | A1 | 8/2009 | Ferrante et al. | |
| 2009/0248025 | A1 * | 10/2009 | Haidukewych | A61B 17/744 606/67 |
| 2009/0306666 | A1 | 12/2009 | Czartoski et al. | |
| 2009/0318981 | A1 * | 12/2009 | Kang | A61B 17/7098 606/329 |
| 2010/0179551 | A1 * | 7/2010 | Keller | A61B 17/744 606/67 |
| 2010/0191240 | A1 * | 7/2010 | Prager | A61B 17/72 606/64 |
| 2010/0268229 | A1 * | 10/2010 | Siravo | A61B 17/72 606/64 |
| 2010/0318085 | A1 * | 12/2010 | Austin | A61B 17/0642 606/62 |

(56) References Cited

U.S. PATENT DOCUMENTS

| | | | |
|---|---|---|---|
| 2010/0331842 A1* | 12/2010 | Milbank | A61B 17/6416 606/62 |
| 2011/0046625 A1* | 2/2011 | Boileau | A61B 17/72 606/64 |
| 2011/0060337 A1 | 3/2011 | Ferrante et al. | |
| 2011/0060373 A1* | 3/2011 | Russell | A61B 17/0401 606/304 |
| 2011/0106080 A1 | 5/2011 | Schlienger et al. | |
| 2011/0137313 A1* | 6/2011 | Jensen | A61B 17/72 606/64 |
| 2011/0196369 A1 | 8/2011 | Osman | |
| 2011/0295254 A1* | 12/2011 | Brunnarius | A61B 17/7258 606/64 |
| 2012/0109128 A1 | 5/2012 | Frigg | |
| 2012/0116400 A1 | 5/2012 | Yang et al. | |
| 2012/0123415 A1* | 5/2012 | Vienney | A61B 17/7098 606/62 |
| 2012/0143192 A1 | 6/2012 | Watanabe et al. | |
| 2012/0150187 A1 | 6/2012 | Gotfried | |
| 2012/0157997 A1* | 6/2012 | Sohngen | A61B 17/744 606/64 |
| 2012/0172875 A1 | 7/2012 | Coati et al. | |
| 2012/0197255 A1* | 8/2012 | Elghazaly | A61B 17/725 606/64 |
| 2012/0209268 A1* | 8/2012 | Overes | A61B 17/1725 606/62 |
| 2012/0226278 A1* | 9/2012 | Nardini | A61B 17/7241 606/64 |
| 2012/0245642 A1* | 9/2012 | Giannoudis | A61B 17/1725 606/280 |
| 2013/0274747 A1* | 10/2013 | Fagan | A61B 17/7266 606/64 |
| 2014/0194877 A1* | 7/2014 | Mangiardi | A61B 17/7258 606/62 |
| 2014/0243827 A1* | 8/2014 | Boileau | A61B 17/7241 606/64 |
| 2015/0038968 A1* | 2/2015 | Vega | A61B 17/744 606/64 |
| 2016/0022336 A1* | 1/2016 | Bateman | A61B 17/8033 606/297 |

OTHER PUBLICATIONS

International Search Report for PCT/IB2009/053468 dated Nov. 13, 2009 in 6 pages.

Office Action for U.S. Appl. No. 12/990,772 dated Oct. 10, 2012 in 12 pages.

* cited by examiner

SURGICAL TECHNIQUE AND APPARATUS FOR PROXIMAL HUMERAL FRACTURE REPAIR

CROSS REFERENCE TO RELATED APPLICATIONS

This application is a divisional of U.S. application Ser. No. 12/990,772, filed Nov. 2, 2010, which is a national phase application of PCT/IB2009/053468, filed pursuant to 35 U.S.C. §371, which claims priority to U.S. provisional patent application 61/051,320, filed May 7, 2008, both of which are herein incorporated by reference in their entireties.

FIELD OF THE INVENTION

The present invention relates to a method and apparatus for fixation of proximal humeral fractures. In particular, the present invention relates to a humeral nail for reduction and orientation of the tuberosities at a humeral fracture site.

BACKGROUND OF THE INVENTION

Figure 1:
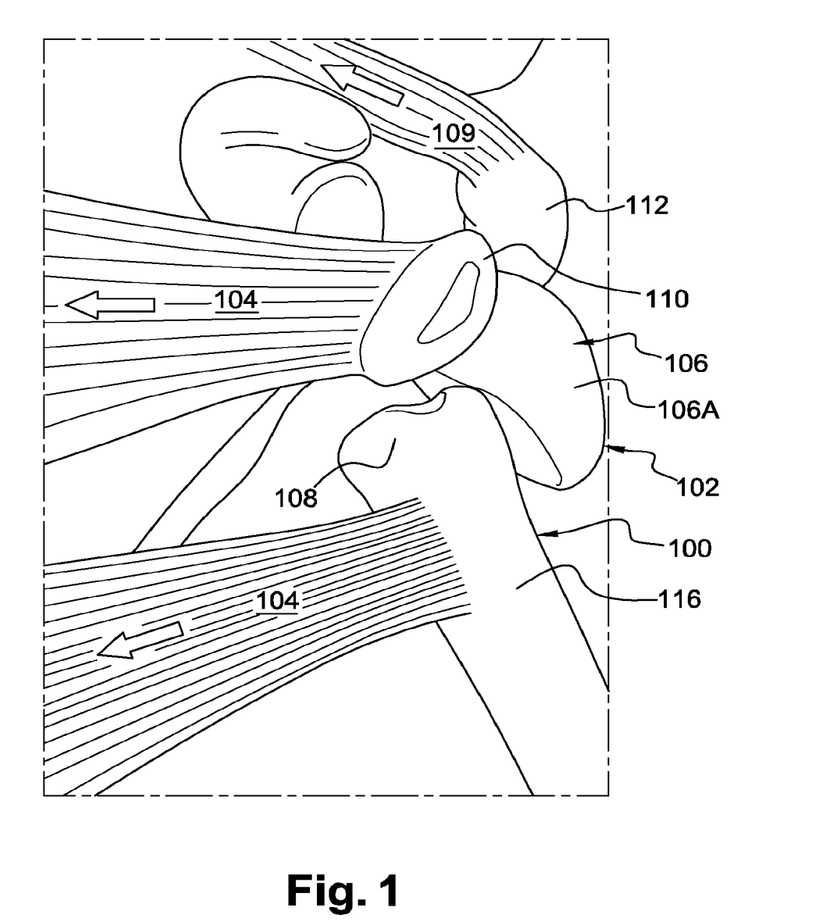
FIG. 1 is a perspective view of an exemplary proximal humeral fracture.

As illustrated in FIG. 1, the humerus 100 of the upper arm is part of a "ball and socket" joint at the shoulder 102. The proximal humerus 102 includes a large rounded humeral head 106 joined to the humerus shaft 116 by a humeral neck 108 and two eminences, the greater and lesser tuberosities 110, 112.

Proximal humeral fractures are the most common humeral fractures. These are often found in patients who have fallen on their arms, creating an axial load on the humerus 100 that causes a fracture of the humeral head 106. In a two-part fracture, the humeral head 106 or a single portion of the head is broken from the humeral shaft 116. In more severe fractures, the humeral head 106 tends to fracture from one or both of the tuberosities 110, 112. As illustrated in FIG. 1, upon occurrence of a fracture the muscles 104 attached to the tuberosities 110, 112 and the humeral shaft 116 pull the humeral head 106, tuberosities 110, 112, and humeral shaft 116 in the directions indicated and away from the correct anatomical positions.

To repair a complex fracture such as illustrated in FIG. 1, a separate reduction device is used to position and retain one or more of the humeral head 106, tuberosities 110, 112, and humeral shaft 116 in the correct anatomical position. As used herein, "reduce" or "reduction" refers to positioning a bone fragment to an anatomically optimal position.

The humeral head 106, tuberosities 110, 112, and humeral shaft 116 are then secured using conventional techniques such as external fixation, percutaneous pinning, plating, intramedullary nailing, shoulder arthroplasty, and others. These methods, however, are not entirely suitable for treatment of more complex fractures, or when tissues are weakened by disease. In these cases, surgical replacement of the shoulder joint is often required.

U.S. Pat. No. 5,472,444 (Huebner et al.) discloses use of a humeral nail for fixation of proximal humeral fractures. Huebner provides an elongated tapered nail or rod having an elongated body with a curved tapered shank that may be secured within a proximal portion of the humeral shaft, with a contiguous proximal portion of the nail extending proximally from the shank to provide a solid foundation to which the humeral head fragments may be secured. The proximal portion has transverse holes oriented at selected angles to receive fasteners attached to the fragments. Huebner does not, however, provide a mechanism to reduce the fracture and retain the fragments during fixation. Also, if a screw is not accurately located in the fragment, Huebner does not provide a mechanism to adjust the location of the fragment relative to the humeral head.

SUMMARY OF THE INVENTION

The present invention relates to a system and method for repairing a proximal humeral fracture using a humeral nail for both reduction and retention of the fragments to the correct anatomical position. The system and method provides for limited rotation of the humeral nail within the medullary canal to adjust the position of a bone fragment relative to the humeral head.

In the preferred embodiment, the procedure is performed entirely percutaneously without the use of a reduction device. Small incisions are made in the skin at selected locations, rather than requiring the entire shoulder joint to be exposed. The humeral nail can be inserted percutaneously, with minimal risk of damage to the rotator cuff. The positioning of the proximal screws limits interference with the articular surface of the humeral head. In the preferred embodiment, no screws are required to retain the humeral head in its anatomical position. Rather, the humeral head is retained medially by the glenoid, anteriorly and posteriorly by the rotator cuff muscles and the tuberosities and superiorly by rotator cuff muscle.

An aiming device is required to position the screws to engage with the corresponding bores in the humeral nail. In one embodiment, the aiming device is attached to the humeral nail. The aiming device is preferably constructed from a radiolucent material to permit imaging when reconstructing the fracture and locating the nail and the screws. In another embodiment, the aiming device involves various imaging techniques. As used herein, "imaging" refers x-ray, MRI, CAT-scan, ultrasound, fluoroscopy, and the like. As used herein, "aiming device" refers to both mechanical devices and imaging devices.

The humeral nail is positioned in the medullary canal in the humerus. The humeral nail is preferably substantially straight which permits it to rotate after insertion in the medullary canal and helps avoid the need to insert the nail through the insertion of the cuff. A first proximal screw is used to move one of the greater or lesser tuberosities fragmented from the humerus toward the humeral nail. The distal tip of the first proximal screw is preferably not advanced substantially beyond the humeral nail. Consequently, the fragment of the greater or lesser tuberosity attached to the humeral nail and the humeral nail itself can be rotated without damaging surrounding bony structures and soft tissues. After the initial movement of the fragment of the greater or lesser tuberosity by the first proximal screw, the attached fragment of the greater or lesser tuberosity is reduced by rotation with the humeral nail to an anatomically optimum position.

The present invention is also directed to a method of reattaching a bone fragment separated from a proximal humerus in a shoulder joint. The method includes introducing a distal end of the humeral nail into a medullary canal of the humerus. A first proximal screw is engaged with the bone fragment and a first proximal bore in the proximal end of the humeral nail to attach the bone fragment to the humeral nail. The humeral nail and the attached bone fragment are rotated relative to the medullary canal of the humerus to position the bone fragment to an anatomically optimal location. The bone fragment is preferably one of the tuberosities.

The humeral nail is optionally rotationally oriented relative to the bone fragment before engaging the first proximal screw. An aiming device is optionally used to locate the first proximal screw relative to the humeral nail. In one embodiment, the aiming device is attached to a proximal end of the humeral nail.

The first proximal screw is preferably advanced in the first proximal bore so that a distal end of the first proximal screw does not substantially extend past the humeral nail. A second proximal screw is engaged with the proximal humerus and a second proximal bore in the proximal end of the humeral nail to prevent further rotation of the humeral nail. The entire procedure is preferably performed percutaneously. The humeral head is preferably retained laterally and inferiorly by the tuberosities, medially by a glenoid of the shoulder joint, and superiorly, anteriorly and posteriorly by a rotator cuff tendon of the shoulder joint, without the use of screws. That is, the humeral head is retained to the proximal humerus solely with anatomical features of the shoulder joint.

The present invention is also directed to a method of reattaching a bone fragment to the proximal humerus. The method includes attaching an aiming device to a proximal end of a substantially straight humeral nail. A distal end of the humeral nail is introduced into a medullary canal of the humerus. An aiming device is used to locate a first proximal screw through the bone fragment, into the proximal humerus, and into a first proximal bore in the proximal end of the humeral nail. The first proximal screw is advanced into the first proximal bore to stabilize the bone fragment relative to the humeral nail and, in some embodiments, to bring the bone fragment into engagement with the proximal humerus. The distal end of the first proximal screw preferably does not substantially extend past the humeral nail. The humeral nail is then rotated within the medullary canal of the humerus so that the bone fragment is reduced to an anatomically optimal location. A second proximal screw is engaged with the proximal humerus and a second proximal bore in the proximal end of the humeral nail to prevent further rotation of the humeral nail.

In one embodiment, the first proximal screw is shorter than a conventional fixation screw so as to not extend substantially beyond the humeral nail and interfere with rotation of the attached fragment and the humeral nail. That is, the screw is of adequate length to traverse the distance from the cortical wall to the humeral nail. In another embodiment, the first proximal screw is only partially advanced into the first proximal bore in the humeral nail. Only after reduction of the fragment through rotation of the humeral nail to an anatomically optimal location is the first proximal screw advanced the remainder of its length.

An aiming device is then used to locate additional screws to reduce and retain other fragments of the humeral head to the humeral nail. The aiming device is also preferably used to locate screws to distally-located bores in the humeral nail. In one embodiment, at least one distal screw is delivered with the forearm in a neutral rotation. The aiming device can be any of a variety of structures that are fixed or rotatable relative to the humeral nail.

One embodiment of the present invention is a humeral nail including a substantially linear elongate shaft having a proximal end and a distal end, a distal bore at the distal end of the elongate shaft and a plurality of proximal bores at the proximal end of the elongate shaft.

In some embodiments, a neutral axis is an intersection of a horizontal plane with a frontal plane containing a central axis of the humeral nail. As such, when the arm is in a neutral rotation position, the neutral axis is substantially perpendicular to the forearm. In some embodiments, an angulated location of the proximal screw(s) is measured with respect to the neutral axis.

One proximal bore is optionally positioned at between about 30 degrees and about 40 degrees relative to the neutral axis, also described as the neutral position. Another proximal bore is positioned at between about 90 degrees and about 100 degrees relative to the neutral position. Still another third proximal bore is positioned at between about 50 degrees and about 60 degrees relative to the neutral position.

Terminology such as "first," "second," "third," etc., is used herein to designate particular components being described. Because various components of the embodiments described herein can be positioned in a number of different orientations and in a number of different sequences, this terminology is used for the purposes of illustration and is not intended to be read in a restrictive manner.

DETAILED DESCRIPTION OF THE PREFERRED EMBODIMENT

Figure 2A:
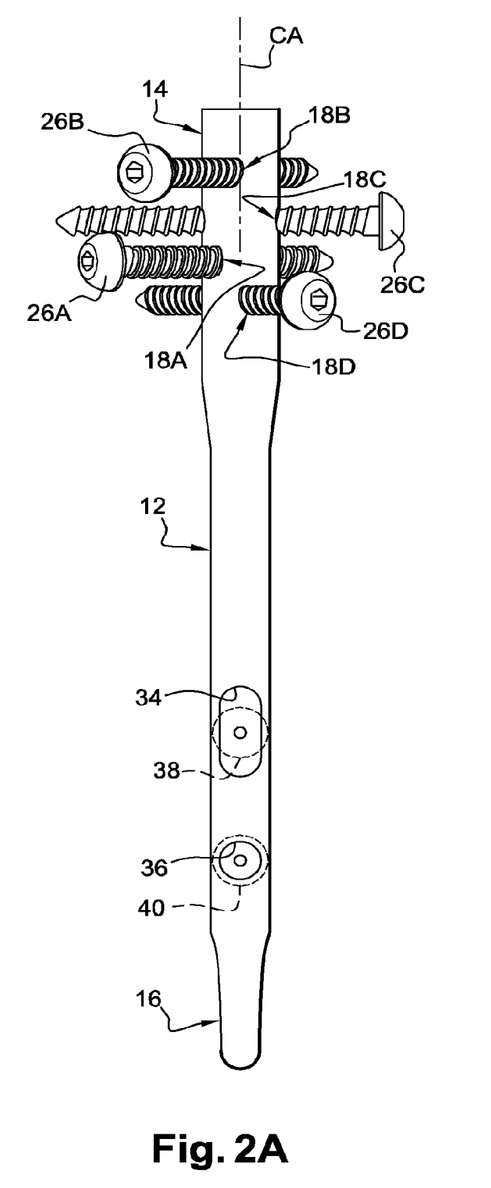
FIG. 2A is a perspective view of a humeral nail in accordance with an embodiment of the present invention.
Figure 2B:
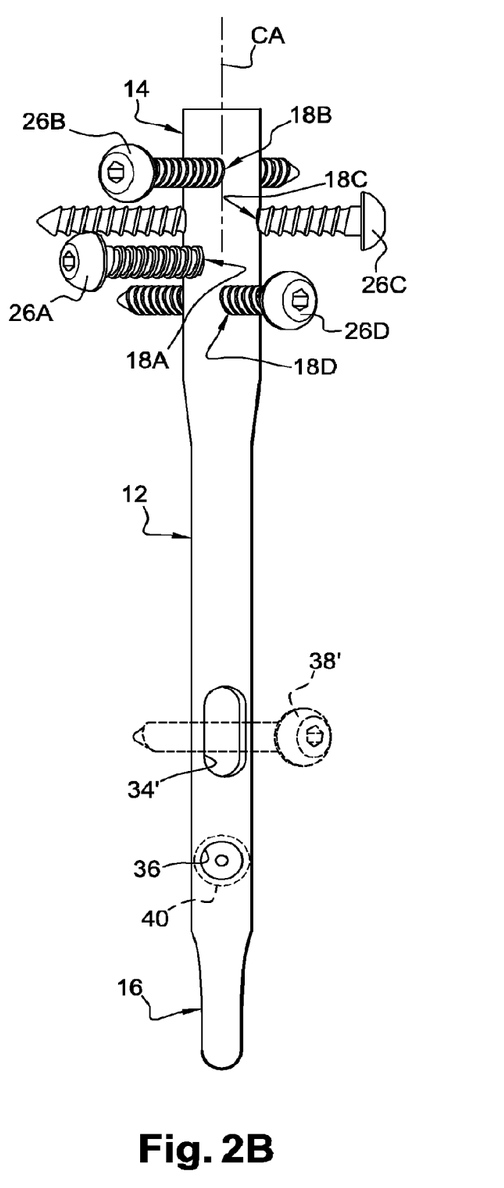
FIG. 2B is a view similar of FIG. 2A, which shows the humeral nail in accordance with another embodiment of the present invention.
Figure 3:
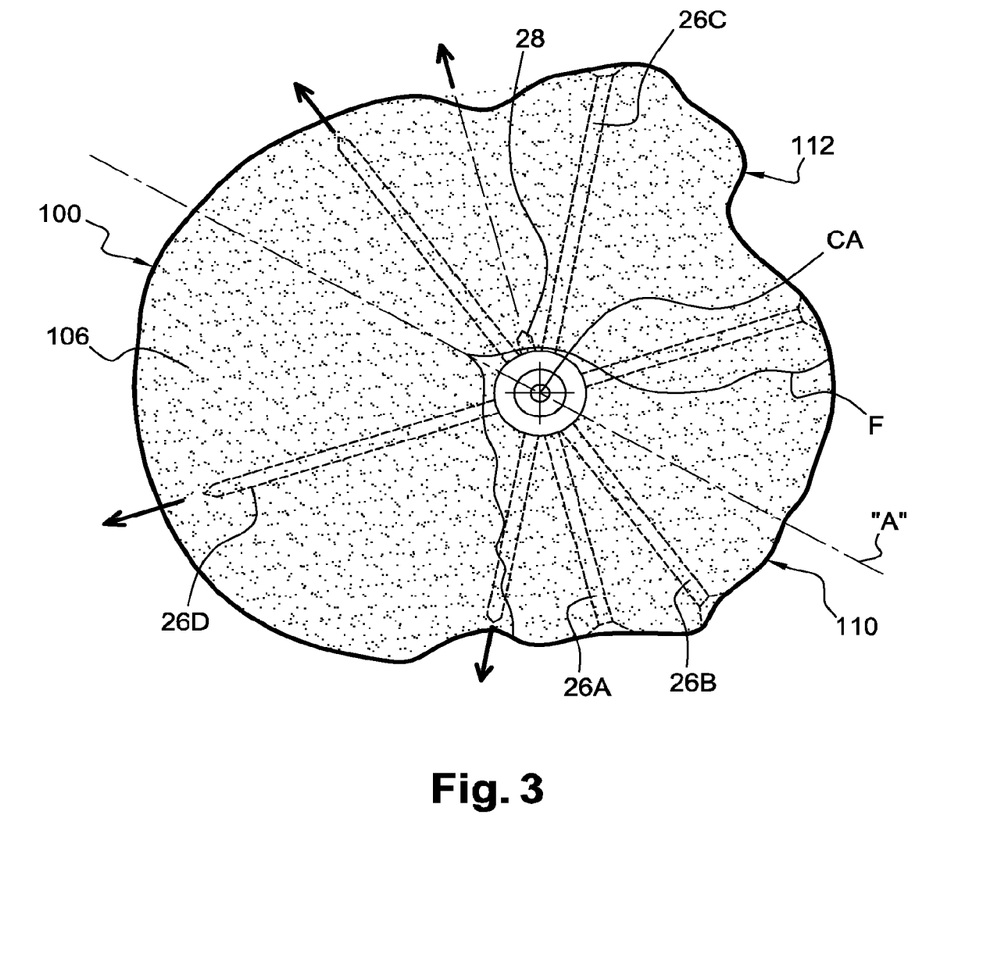
FIG. 3 is a top schematic view of the humeral nail implanted in the humerus in accordance with an embodiment of the present invention.

FIGS. 2A, 2B, 3, 4A-E and 5 show a schematic view of a humeral nail 10. As shown in FIG. 3, this humeral nail is intended to be implanted in the humerus 100, shown in FIG. 1 already described, of a patient to fixate a fracture F at or proximate the greater tuberosity 110 and lesser tuberosity 112 of the proximal humerus. The humeral nail 10 includes a substantially linear shaft 12 having a proximal portion 14 and a distal portion 16. The humeral nail 10 is introduced through the humeral head 106 of the humerus 100 and extends within the humeral shaft 116 such that the distal end 16 of the humeral nail 10 is positioned within the medullary canal of the humeral shaft 116.

It will be noted that the shown humeral nail 10 is designed to be implanted in the right humerus of a patient. A humeral nail that is to be implanted in the left humerus of a patient will be a mirror-image of the humeral nail depicted in the figures.

In the preferred embodiment, small incisions are made in the skin at selected locations, rather than requiring the entire shoulder joint to be exposed. Percutaneous procedures preferably require incisions of less than about 3.81 centimeters, more preferably less than about 2.54 centimeters, and most preferably less than about 1.27 centimeters, although a variety of dimensions are contemplated. The humeral nail 10 can be inserted percutaneously, with minimal risk of damage to the rotator cuff.

Although the humeral nail 10 is primarily discussed as being implanted in a patient's arm to fixate a proximal humeral fracture, the present method and apparatus applies equally well to fractures in other locations of a patient's body without departing from the intended scope of the present invention. For example, the humeral nail 10 may be modified to repair proximal or distal femoral fractures, proximal or distal radial fractures, etc.

In the preferred embodiment, the humeral nail 10 functions similarly to a device for repairing massive rotator cuff tears and is based on reattaching the greater and lesser tuberosities 110, 112 to fixate the fracture F, rather than stabilizing the humeral head 106. The humeral nail 10 is based on the horizontal plane and is thus able to fixate the fracture F without introducing a screw through the articular surface 106A of the humeral head 106. This is accomplished in part by reducing both the tuberosities 110, 112 and providing a stable platform for the humeral head 106. Using this methodology, the humeral nail 10 is designed to treat multi-part fractures (e.g., 2-part, 3-part, 4-part, etc.) in the horizontal plane using a simple and reproducible surgical technique. In addition, the humeral nail 10 can be percutaneously introduced at a location where the humeral head 106 intersects the tuberosities 110, 112, minimizing the invasiveness of the surgery. The fracture F is fixated using particular height and angulation specifications of the humeral nail 10.

FIGS. 2A and 2B show shows a perspective view of the humeral nail 10 in accordance with two embodiments of the present invention. FIG. 3 shows a top schematic view of the humeral nail 10 implanted in the humerus 100. FIGS. 2A, 2B and 3 will be discussed in conjunction with one another.

The shaft 12 of the humeral nail 10 is substantially linear and has a central axis CA extending through a length of the humeral nail 10. The substantially linear shape of the shaft 12 allows the humeral nail 10 to be rotated within the medullary canal without damaging surrounding bone and soft tissue. The proximal portion 14 of the humeral nail 10 includes a first proximal bore 18A, a second proximal bore 18B, a third proximal bore 18C and optionally, a fourth proximal bore 18D. The proximal bores 18A-18D are spaced from a proximal end 23 of the humeral nail 10 and each other at particular heights and angles to permit fixation of the fracture F at the humeral head 106. The third proximal bore 18C is positioned below the second proximal bore 18B, the first proximal bore 18A is positioned below the third proximal bore 18C and the fourth proximal bore 18D is positioned below the first proximal bore 18A, although a variety of respective heights and spacings are contemplated.

In one embodiment, the humeral nail 10 is formed of a bioresorbable material such as polylactide so that the humeral nail 10 does not have to be removed after the fracture F has healed. The humeral nail 10 may optionally be coated with a bone in-growth friendly coating, such as hyaluronate to facilitate cell proliferation and migration, or with an anti-septic coating, such as cement with an antibiotic.

The humeral nail 10 also includes a first proximal screw 26A that is engageable with the first proximal bore 18A, a second proximal screw 26B that is engageable with the second proximal bore 18B, a third proximal screw 26C that is engageable with the third proximal bore 18C and a fourth proximal screw 26D that is engageable with the fourth proximal bore 18D. Each of the screws 26A-26D includes a head portion and a body portion.

In the illustrated embodiment, the head portion has a diameter that is about two times greater than a diameter of the body portion and has a substantially flat surface that is connected to the body portion. This design distributes pressure on the humerus 100 more uniformly. The body portion of each of the proximal screws 26A-26D is optionally threaded to aid in maintaining each of the screws 26A-26D within the proximal bores 18A-18D, respectively.

As can particularly be seen in FIG. 3, the lengths of the body portions of the screws 26A-26D may vary in length depending on the anatomy of the patient. The body portion of the first proximal screw 26A enters at the greater or lesser tuberosity 110, 112 depending on the location of the fracture F, and preferably has a length such that when fully inserted into the humeral nail 10, the body portion of the distal end 28 of the first proximal screw 26A does not substantially extend beyond the humeral nail 10. Thus, the first proximal screw 26A will affix a fragment of the greater or lesser tuberosity 110, 112 to the humeral nail 10, but will not extend to the other side of the humeral nail 10.

If the distal end 28 of the first proximal screw 26A extends beyond through the humeral nail 10, the body portion may catch soft tissue and bone if the humeral nail 10 is rotated within the humerus 100. Generally, the length of the body portion of the first proximal screw 26A is sufficient to extend from the cortical wall of the greater or lesser tuberosity 110, 112 to the central axis CA of the humeral nail 10. In one embodiment, the first proximal screw 26A is between about 25 millimeters (mm) and about 40 mm long. Because the humeral nail 10 is substantially linear and the body portion of the first proximal screw 26A does not extend substantially past the humeral nail 10, the humeral nail 10 with the attached bone fragment of the greater or lesser tuberosity 110, 112 can be rotated within the medullary canal M before additional screws, e.g., proximal screws 26B-26D and distal screws 38, 40 are inserted into the humeral nail 10.

Each of the body portions of the second, third and fourth proximal screws 26B-26D has a length sufficient to pass through its respective bore 18B-180 to the opposite side of the humeral nail 10. The lengths of the body portions of the second, third and fourth proximal screws 26A-26D may have varying lengths, but are generally longer than the first proximal screw 26A.

The first and second proximal screws 26A, 26B are positioned through the fragment of the greater or lesser tuberosity 110, 112 and function to reduce the fragment of the greater or lesser tuberosity 110, 112 and hold the fracture F together. Together, the proximal end 23 of the humeral nail 10 and the first, second and third proximal screws 26A-26C maintain the tuberosities 110, 112 and stabilize the fracture F.

In one embodiment, the proximal end 23 of the humeral nail 10 and the second and third proximal screws 26B, 26C are positioned in a triangular formation such that the fracture F is stabilized by three points: the proximal end 23 of the humeral nail 10, the second proximal screw 268 positioned through a posterior part of the greater or lesser tuberosity 110, 112 and the third proximal screw 26C positioned through an anterior part of the greater or lesser tuberosity 110, 112. In this configuration, the fracture F is maintained laterally and inferiorly by the tuberosities 110, 112; medially by the glenoid; and superiorly, anteriorly and posteriorly by the rotator cuff tendon, without requiring the fourth proximal screw 26D. In addition, the angulation between the first proximal screw 26A through the greater tuberosity 110 and the lesser tuberosity 112 is wide enough to reduce the greater or lesser tuberosity 110, 112 and rotate the humeral nail 10 without damaging the surrounding bone structures or soft tissues. The angulation is also wide enough to avoid cuff insertion when inserting the humeral nail 10 in the humerus 100 and still catch the greater tuberosity 110 and lesser tuberosity 112 at their centers.

The fourth proximal screw 26D functions to support the humeral head 106 and locks the humeral head 106 in position. While the humeral nail 10 is discussed as including a fourth proximal bore 18D and a fourth proximal screw 26D, the fourth proximal bore and screw 18D, 26D are not necessary for the humeral nail 10 to properly function and are thus optional. In the preferred embodiment, no screws are used to secure the humeral head 106. In particular, the humeral head 106 is retained laterally and inferiorly by the tuberosities 110, 112, medially by the glenoid and superiorly, anteriorly and posteriorly by the rotator cuff tendon (see FIG. 1).

Referring back to FIGS. 2A and 2B, the distal portion 16 of the humeral nail 10 includes a first distal bore 34 or 34' and a second distal bore 36. In the embodiment of FIG. 2A, the distal bores 34 and 36 are spaced from one another but lie along the same axial line. In the preferred embodiment of FIG. 2B, the distal bores 34' and 36 are not lying along the same axial line. In some embodiments, a neutral axis A is an intersection of a horizontal plane with a frontal plane containing a central axis CA of the humeral nail 10. As such, when the patient's arm is in a neutral rotation position, the neutral axis A is substantially perpendicular to the forearm. In the embodiments of FIGS. 2A and 2B, the neutral axis A is substantially parallel with an axis passing through each of the distal bores 34 and 36 and is substantially perpendicular to the central axis CA, whereas the axis of the distal bore 34' is at a non zero angle relative to the neutral axis in either the postero-anterior direction or the antero-posterior direction. In a preferred embodiment, one of the distal bore axes is preferably parallel to the neutral axis. In the vertical plane, the distal bore axis is angulated relative to the central axis CA. In another preferred embodiment, in the vertical plane, the distal bore axis is preferably perpendicular to the central axis CA. As described the angular locations of the screws 26A-26D are indicated relative to the neutral axis A.

A first distal screw 38 or 38' is engageable with the first distal bore 34 or 34' along the axis of the distal bore. A second distal screw 40 is engageable with the second distal bore 36 along the axis of the distal bore. The distal screws 38 or 38' and 40 are preferably designed such that one is static and the other is dynamic. The first and second distal screws 38 or 38' and 40 are in dotted lines in FIGS. 3A and 3B so that the first and second distal bores 34 or 36' and 36 can be seen.

Figure 4A:
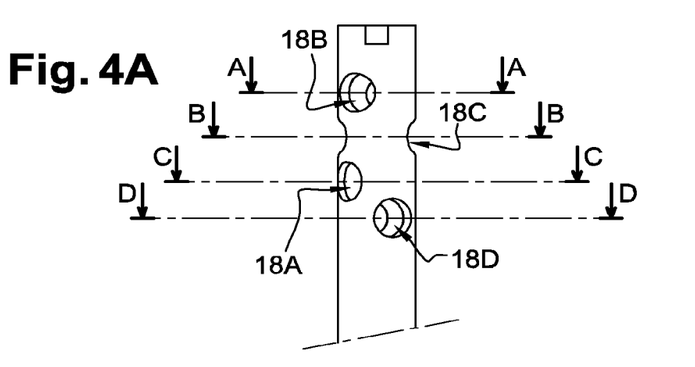
FIG. 4A is a schematic view of a proximal end of the humeral nail in accordance with an embodiment of the present invention.
Figure 4B:
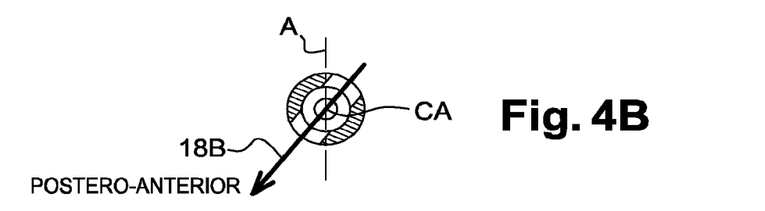
FIG. 4B is a top cross-sectional view through lines A-A of FIG. 4A of the location of a second proximal bore of the humeral nail in accordance with an embodiment of the present invention.
Figure 4C:
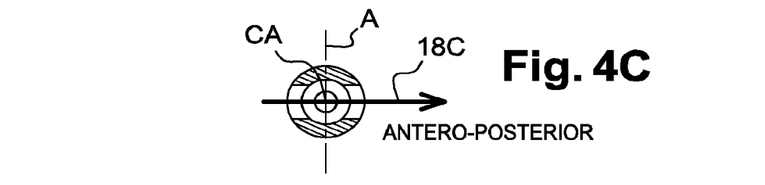
FIG. 4C is a top cross-sectional view through lines B-B of FIG. 4A of the location of a third proximal bore of the humeral nail in accordance with an embodiment of the present invention.
Figure 4D:
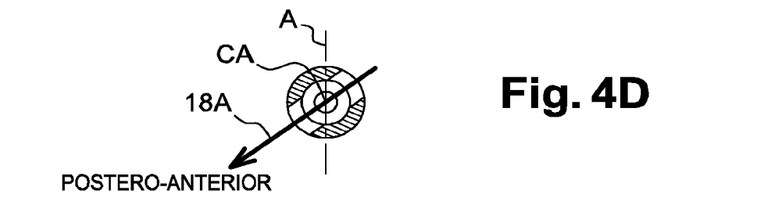
FIG. 4D is a top cross-sectional view through lines C-C of FIG. 4A of the location of a first proximal bore of the humeral nail in accordance with an embodiment of the present invention.
Figure 4E:
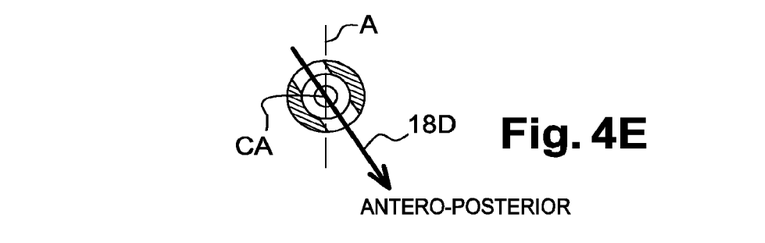
FIG. 4E is a top cross-sectional view through lines D-D of FIG. 4A of the location of a fourth proximal bore of the humeral nail in accordance with an embodiment of the present invention.

FIG. 4A shows a schematic view of the proximal portion 14 of the humeral nail 10 and will be discussed in conjunction with FIGS. 4B, 4C, 4D, 4E, and 5. FIG. 4B shows a top cross-sectional view through lines A-A of FIG. 4A of the location of the second proximal bore 18B, FIG. 4C shows a top cross-sectional view through lines B-B of FIG. 4A of the location of the third proximal bore 18C, FIG. 4D shows a top cross-sectional view through lines C-C of FIG. 4A of the location of the first proximal bore 18A and FIG. 4E shows a top cross-sectional view through lines D-D of FIG. 4A of the location of the fourth proximal bore 18D.

As previously mentioned, the proximal bores 18A-18D are positioned at particular heights and angles relative to the neutral axis A. The particular heights and angles allow the humeral nail 10 to bring the greater or lesser tuberosity 110, 112 of the humerus 100 back to its anatomical position without damaging the humeral shaft 116 and surrounding soft tissue. The proximal bores 18A-18D are positioned in a postero-anterior or antero-posterior direction, also described as either internally or externally, relative to the neutral axis A of the humeral nail 10. When the proximal bore 18A-18D is positioned internally relative to the neutral axis A, the proximal bore 18A-18D is located in a first direction from the neutral axis A. When the proximal bore 18A-18D is positioned externally relative to the neutral axis A, the proximal bore 18A-18D is located in a second direction from the neutral axis A.

Figure 5:
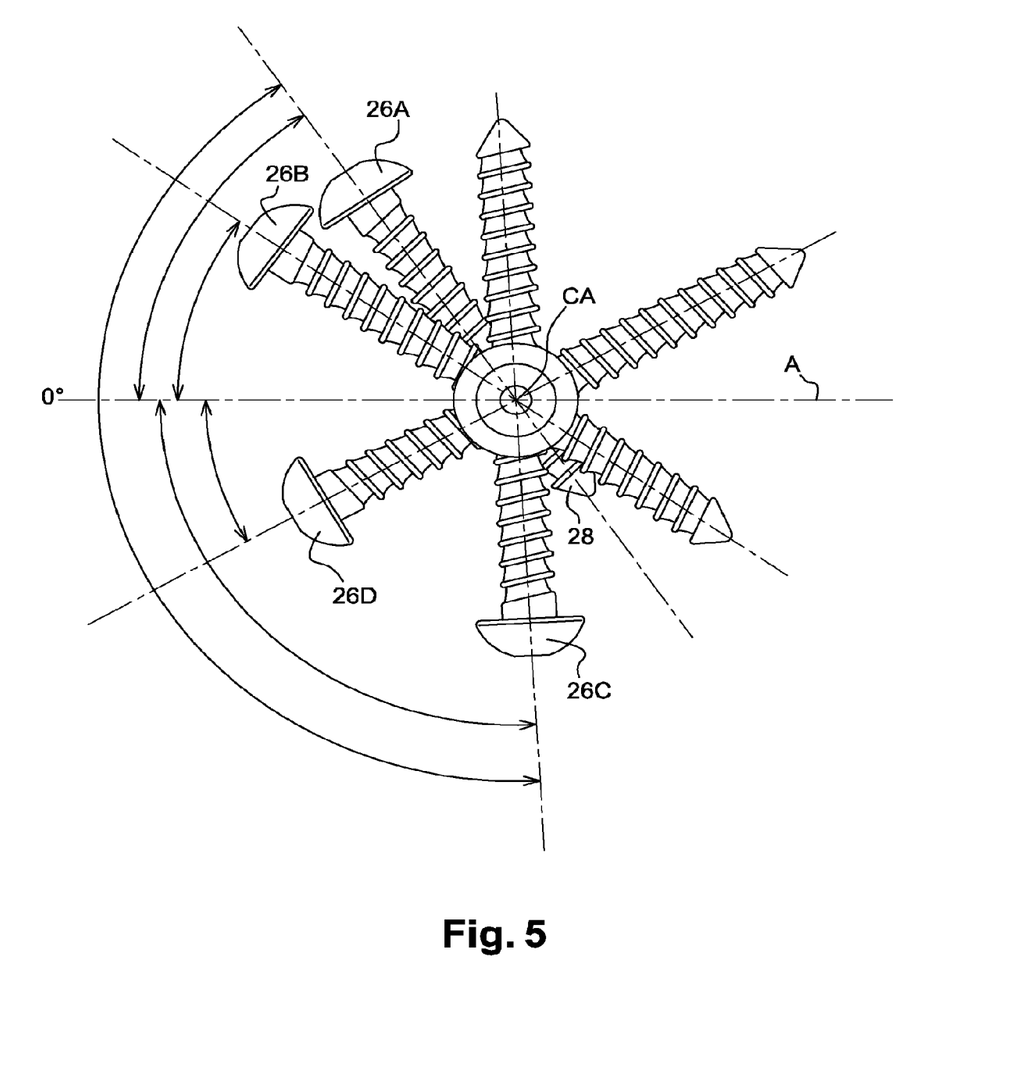
FIG. 5 is a top view showing the respective angular offsets of a plurality of proximal screws in accordance with an embodiment of the present invention.

In the embodiment shown in FIG. 5, the second proximal bore 18B is located between about 7 millimeters (mm) and about 11 mm from the proximal end 23 of the humeral nail 10 and at an angle relative to the neutral axis A about 30 degrees and 40 degrees, particularly about 9 mm from the proximal end 23 of the humeral nail 10 and at an internal rotation of about 35 degrees. In one embodiment, the third proximal bore 18C is located between about 13 mm and about 17 mm from the proximal end 23 of the humeral nail 10 and at an external rotation of between about 90 degrees and 100 degrees, particularly about 15 mm from the proximal end 23 of the humeral nail 10 and at an external rotation of about 95 degrees. In one embodiment, the first proximal bore 18A is located between about 19 mm and about 23 mm from the proximal end 23 of the humeral nail 10 and at an internal rotation of between about 50 degrees and 60 degrees, particularly about 21 mm from the proximal end 23 of the humeral nail 10 and at an internal rotation of about 55 degrees. In one embodiment, the fourth proximal bore 18D is located between about 24 mm and about 28 mm from the proximal end 23 of the humeral nail 10 and at an external rotation of between about 25 degrees and 35 degrees, particularly about 26 mm from the proximal end 23 of the humeral nail 10 and at an external rotation of about 30 degrees. Besides, the axis of the distal bore 34' is at an external rotation of between 15 degrees to 25 degrees relative to the neutral axis A.

In some embodiments, the angles as described above causes the screw axes to not only be in the tuberosities, but also at the insertion of the rotator cuff on the tuberosities. This can be particularly useful in patients with weak bones, where a screw would only be inserted into bone which it would otherwise pass through without being retained. Instead, and in accordance with some embodiments described herein, the angular offsets and relative positions of the screws facilitate insertion at the insertion muscle location, where the screws are retained by more solid bone and the muscle itself.

The method for reducing and orienting the tuberosities 110, 112 at a humeral fracture site will now be described in detail.

The humeral nail 10 is introduced through the humeral head 106 and into the medullary canal of the humerus 100. The humeral nail 10 is preferably inserted in a region of the humeral head 106 offset from the articular surface 106A. In one embodiment, the humeral nail 10 is introduced into the humerus 100 percutaneously or using a small superior trans-deltoid approach. The humeral nail 10 is preferably substantially straight which permits it to rotate after insertion in the medullary canal.

After the humeral nail 10 is positioned within the humerus 100, an aiming device is used to locate the first proximal screw 26A in one of the greater or lesser tuberosities 110, 112 and into the first proximal bore 18A. In one embodiment, an aiming device is attached to the humeral nail 10. The aiming device is preferably fixed relative to the central axis CA of the humeral nail, although a rotating aiming device may be used. In one embodiment, the aiming device is formed of a radiolucent material and allows the surgeon to see the fracture reconstruction, the location of the humeral nail 10 and the location of the proximal and distal screws 26A-26D, 38, 40. In another embodiment, the aiming device is attached to the humeral nail after the humeral nail is introduced into the medullary canal. Alternatively, the aiming device is an imaging device.

The first proximal screw 26A is used to move one of the tuberosities 110, 112 that has been fragmented toward the proximal humerus 102. The distal tip 28 (see FIGS. 3 and 5) of the first proximal screw 26A is preferably not advanced substantially beyond the humeral nail 10. The first proximal screws 26A is not intended to go into the humeral head 106, but rather to the border of the humeral head 106.

Next, the attached fragment of the greater or lesser tuberosity 110, 112 is reduced to an anatomically optimal position by rotation with the humeral nail 10. The fragment of the greater or lesser tuberosity 110, 112 attached to the humeral nail 10 can be rotated clockwise or counterclockwise around the central axis CA without damaging surrounding bony structures and soft tissues. Depending on the condition of the surrounding bony structure, the fragment of the greater or lesser tuberosity 110, 112 and the humeral nail 10 can be rotated between about zero and about 20 degrees, and preferably between about zero and about 40 degrees. In one embodiment, the fragment of the greater or lesser tuberosity 110, 112 is simultaneously moved towards the proximal humerus 102 and rotated toward an anatomically optimal position.

In another embodiment, the first proximal screw 26A is only partially advanced into the first proximal bore 18 in the humeral nail 10. Only after reduction of the fragment of the greater or lesser tuberosity 110, 112 to an anatomically optimal location by rotation of the humeral nail 10 is the first proximal screw 26A advanced the remainder of its length. Once the first proximal screw 26A is advanced into the humeral head 106, further rotation of the humeral nail 10 is not advised. Even in the fully engaged position, the distal end 28 of the first proximal screw 26A preferably does not penetrate the cortical bone on the articular surface 106A.

The aiming device is used to insert the remainder of the proximal screws 26B-26D into the humeral bores 18B, 18C, 18C. Once the proximal screws 26A-26D are secured through the proximal bores 18A-18D, respectively, the first and second distal screws 38, 40 are secured through the first and second distal bores 34, 36, respectively, in the distal portion 14 of the humeral nail 10 using the aiming device.

Various modifications and additions can be made to the exemplary embodiments discussed without departing from the scope of the present invention. For example, while the embodiments descriconcave articular surface above refer to particular features, the scope of this invention also includes embodiments having different combinations of features and embodiments that do not include all of the descriconcave articular surface features. Accordingly, the scope of the present invention is intended to embrace all such alternatives, modifications, and variations as fall within the scope of the claims, together with all equivalents thereof.

What is claimed is:

1. A method of reattaching at least one bone fragment separated from a proximal portion of a humerus in a shoulder joint, the method comprising the steps of:
    introducing a distal end of a humeral nail into a medullary canal of the humerus;
    engaging a first proximal screw with the at least one bone fragment and the humeral nail, wherein a distal end of the first proximal screw does not extend substantially past the humeral nail and a first proximal bore in the proximal end of the humeral nail to attach the bone fragment to the nail,
        wherein the first proximal bore is positioned between about 50 degrees and about 60 degrees relative to a neutral axis in a postero-anterior direction;
    after inserting the first proximal screw into the humeral nail, rotating the humeral nail and the attached bone fragment relative to the medullary canal of the humerus to position the bone fragment such that distal end of the proximal screw does not damage surrounding bony structures and soft tissues;
    engaging a second proximal screw with, the at least one bone fragment and a second proximal bore in the proximal end of the humeral nail to attach the bone fragment to the nail, wherein the second proximal bore is positioned between about 30 degrees and about 40 degrees relative to the neutral axis in a postero-anterior direction; and
    engaging a third proximal screw with the at least one bone fragment and a third proximal bore in the proximal end of the humeral nail to attach the bone fragment to the nail, wherein the third proximal bore is positioned between about 90 degrees and about 100 degrees relative to the neutral axis in an antero-posterior direction, and wherein the first proximal screw has a length shorter than a length of the second and third proximal screws.

2. The method of claim 1, further comprising the step of rotationally orienting the humeral nail relative to the bone fragment before engaging the first proximal screw.

3. The method of claim 1, further comprising the step of using an: aiming device to locate the first proximal screw relative to the humeral nail.

4. The method of claim 1, further comprising the step of attaching an aiming device to a proximal end of the humeral nail.

5. The method of claim L further comprising the step of advancing the first proximal screw in the first proximal bore so that a distal end of the first proximal screw does not substantially extend past the humeral nail.

6. The method of claim 1, further comprising the step of engaging a second proximal screw with the proximal humerus and a second proximal bore in the proximal end of the humeral nail.

7. The method of claim 1, wherein the humeral nail and first proximal screw are implanted percutaneously.

8. The method of claim 1, further comprising the step of engaging a plurality of proximal screws with the proximal humerus and a plurality of proximal bores in the proximal end of the humeral nail.

9. The method of claim 1, further comprising the step of engaging at least one distal screw with the humerus and a distal bore in the distal end of the humeral nail.

10. The method of claim 1, wherein engaging the first proximal screw comprises engaging the first proximal screw with a greater tuberosity of the proximal humerus, into the proximal humerus, and into the first proximal bore in the proximal end of the humeral nail.

11. The method of claim 1, wherein engaging the first proximal screw comprises engaging the first proximal screw with a lesser tuberosity of the proximal humerus, into the proximal humerus, and into the first proximal bore in the proximal end of the humeral nail.

12. The method of claim 1, wherein rotating the humeral nail and the attached bone fragment within the medullary canal of the humerus comprises rotating the humeral nail and the attached bone fragment about zero degrees to about 40 degrees before a second proximal screw is engaged with the humeral nail.

13. The method of claim 1, wherein the first proximal screw, second proximal screw, and third proximal screw are configured to retain a humeral head of the proximal humerus medially by the glenoid, anteriorly and posteriorly by the rotator cuff muscles and the tuberosities, and superiorly by the humeral nail.

14. The method of claim 1, wherein the first proximal screw, second proximal screw, and third proximal screw are configured to retain a humeral head of the proximal humerus to the proximal humerus solely with anatomical features of the shoulder joint.

15. The method of claim 1, wherein the humeral nail comprises a substantially linear shaft.

16. The method of claim 1, wherein the angular offset and relative position of the proximal screw facilitates insertion of the screw at the insertion muscle location, where the screws are retained by substantially solid bone and the muscle.

17. The method of claim 1, wherein the humeral nail includes a central axis that is perpendicular to the neutral axis.

18. The method of claim 17, wherein the first proximal bore is positioned along a first proximal axis, and the first proximal axis is perpendicular to the central axis.

19. The method of claim 17, wherein the second proximal bore is positioned along a second proximal axis, and the second proximal axis is perpendicular to the central axis.

20. The method of claim 17, wherein the third proximal bore is positioned along a third proximal axis, and the third proximal axis is perpendicular to the central axis.

* * * * *

UNITED STATES PATENT AND TRADEMARK OFFICE
CERTIFICATE OF CORRECTION

PATENT NO. : 9,597,128 B2  
APPLICATION NO. : 14/270312  
DATED : March 21, 2017  
INVENTOR(S) : Pascal Boileau et al.

Page 1 of 1

It is certified that error appears in the above-identified patent and that said Letters Patent is hereby corrected as shown below:

In the Specification

At Column 10, Line 4, change "descriconcave" to --of the concave--.

At Column 10, Line 7, change "descriconcave" to --concave--.

In the Claims

At Column 10, Line 58, in Claim 5, change "claim L" to --claim 1,--.

Signed and Sealed this  
Fourth Day of July, 2017

Joseph Matal  
*Performing the Functions and Duties of the*  
*Under Secretary of Commerce for Intellectual Property and*  
*Director of the United States Patent and Trademark Office*